(12) United States Patent
Takaoka et al.

(10) Patent No.: US 6,600,070 B2
(45) Date of Patent: Jul. 29, 2003

(54) METHODS FOR MAKING 2-(ω-ALKOXYCARBONYLALKANOYL)-4-BUTANOLIDE, ESTER OF ω-HYDROXY-(ω-3)-KETOALIPHATIC ACID, AND DERIVATIVES THEREOF

(75) Inventors: Hideaki Takaoka, Chiba (JP); Sigeru Wada, Chiba (JP); Nobuhiko Ito, Chiba (JP); Akio Hasebe, Chiba (JP); Shinzo Imamura, Aichi (JP); Hideo Muraoka, Aichi (JP)

(73) Assignee: Soda Aromatic Co., Ltd. (JP)

( * ) Notice: Subject to any disclaimer, the term of this patent is extended or adjusted under 35 U.S.C. 154(b) by 0 days.

(21) Appl. No.: 09/997,140

(22) Filed: Nov. 29, 2001

(65) Prior Publication Data

US 2002/0068832 A1 Jun. 6, 2002

Related U.S. Application Data

(62) Division of application No. 09/894,014, filed on Jun. 28, 2001, now Pat. No. 6,475,133, which is a division of application No. 09/242,805, filed as application No. PCT/JP98/02930 on Jun. 30, 1998, now Pat. No. 6,291,688.

(30) Foreign Application Priority Data

| Jun. 30, 1997 | (JP) | 9-189021 |
| Jun. 30, 1997 | (JP) | 9-189022 |
| Jul. 25, 1997 | (JP) | 9-215752 |
| Feb. 20, 1998 | (JP) | 10-55827 |

(51) Int. Cl.[7] ............................................. C07C 51/42
(52) U.S. Cl. ............................................. 562/593; 568/410
(58) Field of Search ............................. 562/593; 568/410

(56) References Cited

U.S. PATENT DOCUMENTS

| 5,808,106 A | 9/1998 | Katou et al. |
| 6,291,688 B1 | 9/2001 | Takaoka et al. |

*Primary Examiner*—Paul J. Killos
(74) *Attorney, Agent, or Firm*—Piper Rudnick LLP

(57) ABSTRACT

In industrial production of ω-hydroxyaliphatic acid being an important intermediate for large cyclic lactone-based perfumes, using dicarboxylate ester which is inexpensive and readily obtainable, a method, with high yield and improved selectively, for making a 2-(ω-alkoxycarbonylalkanoyl)-4-butanolide and an alkaline metal salt thereof, an ester of ω-hydroxy-(ω-3)-ketoaliphatic acid as a novel compound and a derivative thereof, and a method for making the same are provided.

Condensation reaction of γ-butyrolactone with a dicarboxylate ester represented by the general formula (1) ROOC(CH$_2$)nCOOR wherein n is an integer of 7 to 13 and R is an alkyl group forms a condensation solution containing an alkaline metal salt of 2-(ω-alkoxycarbonylalkanoyl)-4-butanolide represented by the general formula (3):

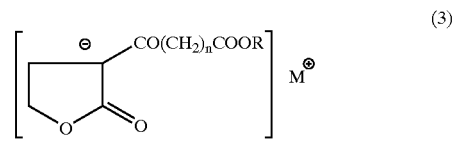

wherein n is an integer of 7 to 13, R is an alkyl group, and M is an alkaline metal; the solution is extracted with water or an aqueous alkaline solution and subjected to hydrolysis and decarboxylation to form an alkaline metal salt of ω-hydroxy-(ω-3)-ketoaliphatic acid represented by the general formula (5):

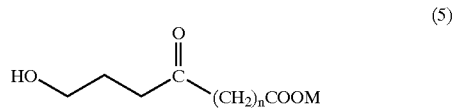

wherein n is an integer of 7 to 13 and M is an alkaline metal; and the compound is selectively and effectively separated and recovered and then acidified to form an ω-hydroxy-(ω-3)-ketoaliphatic acid represented by the general formula (10):

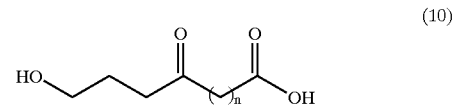

wherein n is an integer of 7 to 13.

4 Claims, No Drawings

METHODS FOR MAKING 2-(ω-ALKOXYCARBONYLALKANOYL)-4-BUTANOLIDE, ESTER OF ω-HYDROXY-(ω-3)-KETOALIPHATIC ACID, AND DERIVATIVES THEREOF

This application is a divisional of application Ser. No. 09/894,014, filed on Jun. 28, 2001 now U.S. Pat. No. 6,475,133, which is a divisional of application Ser. No. 09/242,805, filed on Feb. 24, 1992 now U.S. Pat. No. 6,291,688, which is a 371 of PCT/JP98/02930, filed on Jun. 30, 1998, incorporated herein by reference.

TECHNICAL FIELD

The present invention relates to methods for making 2-(ω-alkoxycarbonylalkanoyl)-4-butanolide and derivatives thereof, novel esters of ω-hydroxy-(ω-3)-ketoaliphatic acid and derivatives thereof, which are useful as a variety of synthetic raw materials and intermediates, and are prepared as intermediates in the production step of ω-hydroxyaliphatic acid being important intermediates of large cyclic lactone-based perfumes in the perfume industry.

The present invention also relates to a method for separating and purifying an alkaline metal salt of 2-(ω-alkoxycarbonylalkanoyl)-4-butanolide and derivatives thereof, and unreacted dicarboxylic ester, in the production of ω-hydroxyaliphatic acid, being an important intermediate of the large cyclic lactone-based perfume.

Furthermore, the present invention relates to a method for separating and recovering ω-hydroxy-(ω-3)-ketoaliphatic acid and salts thereof, dicarboxylic acid and salts thereof, and α,ω-dihydroxy-δ,(ω-3)-alkanedione, in the production of ω-hydroxyaliphatic acid, being an important intermediate of the large cyclic lactone-based perfume.

BACKGROUND ART

Alkaline metal salts of ω-hydroxy-(ω-3)-ketoaliphatic acid represented by the general formula (5):

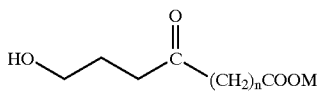

(5)

(wherein n is an integer of 7 to 13, and M indicates an alkaline metal), and ω-hydroxy-(ω-3)-ketoaliphatic acids represented by the general formula (10):

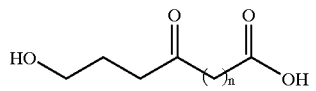

(10)

(wherein n is an integer of 7 to 13) are useful as a variety of synthetic raw materials and intermediates and are particularly important intermediates for macro cyclic lactone-based perfumes in the perfume industry.

2-(ω-Alkoxycarbonylalkanoyl)-4-butanolide is useful as a variety of synthetic raw materials and intermediates and is effectively used as an intermediate in the production of the above-mentioned ω-hydroxyaliphatic acid, which is a particularly important intermediate for large cyclic lactone-based perfumes, such as cyclopentadecanolide and cyclohexadecanolide, in the perfume industry.

Among conventional synthesizing processes for ω-hydroxyaliphatic acid, a method using ω-cyanoundecanoate ester and γ-butyrolactone as starting materials is disclosed in Japanese Patent Application Laid-Open No. Hei 5-86013.

In this method, however, raw materials are generally difficult to prepare, and relatively expensive methyl 11-cyanoundecanoate is used as a raw material. Furthermore, ammonia formed in the final carboxylation step of the nitrile group at the ω-position requires a complicated procedure and adversely affects the scent of the final product; hence this method is still industrially unsatisfactory.

Other synthesizing methods for ω-hydroxyaliphatic acid using α-(ω-cyanoalkanoyl)-γ-butyrolactone as a starting material are disclosed in Japanese Patent Application Laid-Open Nos. 3-11036 and 5-86013. As an advantage of these methods, the intermediate, ω-hydroxyketonitrile, which is prepared by hydrolysis and decarboxylation of α-(ω-cyanoalkanoyl)-γ-butyrolactone in the presence of an alkaline metal hydroxide, is oil-soluble; hence a large amount of water used and alkaline metal carbonate formed as a byproduct are easily separable.

Starting materials for α-(ω-cyanoalkanoyl)-γ-butyrolactone, however, are difficult to obtain. When relatively expensive a ω-cyanoundecanoate ester is used as a raw material or when the nitrile group at the ω-position is finally carboxylated, ammonia forms. Thus, a complicated process is required and ammonia adversely affects the scent of the final product; hence, this method is still industrially unsatisfactory.

PCT Patent Application Laid-Open No. WO97-06156 discloses a method using a significantly readily obtainable and inexpensive dicarboxylate ester represented by the general formula ROOC(CH$_2$)$_n$COOR, wherein n is an integer of 7 to 13 and R is an alkyl group, and γ-butyrolactone as starting materials. In this method, an excess of dicarboxylate ester is mixed with γ-butyrolactone in the presence of a basic condensing agent at room temperature and is heated and stirred under normal pressure while removing methanol formed in the reaction to prepare 2-(ω-alkoxycarbonylalkanoyl)-4-butanolide. This method is also excellent.

The selectivity and yield, however, is still unsatisfactory. Furthermore, a large excess of aqueous alkaline solution must be added during hydrolysis and decarboxylation of the intermediate, 2-(ω-alkoxycarbonylalkanoyl)-4-butanolide. Thus, a disadvantage of the method is removal of the large amount of water by distillation before the subsequent Wolff-Kishner reduction step.

In this method, an excess of dicarboxylate ester which is two times or more the fed amount of γ-butyrolactone is used to increase the selectivity on the basis of the dicarboxylate ester raw material represented by the above-mentioned general formula, and unreacted dicarboxylate ester is recovered from the reaction mixture to reuse in the next reaction.

In the separation of the unreacted dicarboxylate ester and 2-(ω-alkoxycarbonylalkanoyl)-4-butanolide after the reaction, after acidification of the condensation solution, extraction with a solvent such as ethyl acetate, washing, and recovery of the solvent, the reaction mixture is subjected to simple distillation so that the unreacted dicarboxylate ester in the distilled section is separated from the condensation product, 2-(ω-alkoxycarbonylalkanoyl)-4-butanolide, in the distillation residue.

This method, however, requires a complicated process including many steps, such as extraction and simple distillation, and has a problem of decomposition of 2-(ω-alkoxycarbonylalkanoyl)-4-butanolide in the distillation.

Furthermore, in the subsequent alkaline hydrolysis, decarboxylation, and Wolff-Kishner reduction, the method requires a complicated step in which alkaline is readded to 2-(ω-alkoxycarbonylalkanoyl)-4-butanolide obtained by the acidification.

Japanese Patent Application Laid-Open No. Hei 4-134047 discloses a method for separating three types of mixtures, that is, ω-hydroxyaliphatic acid or its ester, α-ω-diol, and dicarboxylic acid or its ester, but does not suggest a compound having a carbonyl group in the molecule.

DISCLOSURE OF THE INVENTION

The present inventors have intensively researched solutions to the problems in the method disclosed in the PCT Patent Application Laid-Open No. WO97-06156, that is, the use of a large amount of aqueous alkaline solution and a large amount of heat, and the laborious steps for separating water, and have discovered that these problems may be solved by using a novel compound, an ester of ω-hydroxy-(ω-3)-ketoaliphatic acid, as an intermediate in the production of ω-hydroxyaliphatic acid, and have thereby completed the present invention.

It is an object of the present invention to provide methods, with high yield, improved selectively, and industrial advantages, for making 2-(ω-alkoxycarbonylalkanoyl)-4-butanolide and its derivatives, such as an alkaline metal salt, using readily obtainable and inexpensive dicarboxylate ester.

The present inventors have also discovered a method for effectively separating the condensation products, alkaline metal of 2-(ω-alkoxycarbonylalkanoyl)-4-butanolide and its derivative from the unreacted ester by extraction using an inactive solvent with water or an aqueous alkaline solution or by solid-liquid separation using an inactive solvent in the separation of the reaction product and the unreacted dicarboxylate ester from the condensation solution which is prepared from γ-butyrolactone and an excess of dicarboxylate ester in the presence of a base, and have completed the present invention.

It is another object of the present invention to provide a novel compound, ester of ω-hydroxy-(ω-3)-ketoaliphatic acid, which is advantageously used as an intermediate in the industrial production of ω-hydroxyaliphatic acid being an important intermediate for a large cyclic lactone-based perfume, and to provide a method for producing with high yield the ester of ω-hydroxy-(ω-3)-ketoaliphatic acid and derivatives thereof.

It is a further object of the present invention to provide a method for separating and recovering highly selectively ω-hydroxy-(ω-3)-ketoaliphatic acid and salts thereof, dicarboxylic acid and salts thereof as byproducts, and α,ω-dihydroxy-δ,(ω-3)-alkanedione, in the industrial production of ω-hydroxyaliphatic acid, being an important intermediate for a large cyclic lactone-based perfume.

The present invention, for achieving the above-mentioned objects, provides a method for making 2-(ω-alkoxycarbonylalkanoyl)-4-butanolide represented by the general formula (2) and an alkaline metal salt of the 2-(ω-alkoxycarbonylalkanoyl)-4-butanolide represented by the general formula (3) comprising condensation reaction of γ-butyrolactone with a dicarboxylate ester represented by the general formula (1):

$$ROOC(CH_2)_nCOOR \quad (1)$$

wherein n is an integer of 7 to 13 and R is an alkyl group;

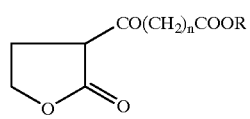
(2)

wherein n is an integer of 7 to 13 and R is an alkyl group;

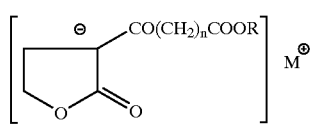
(3)

wherein n is an integer of 7 to 13, R is an alkyl group, and M is an alkaline metal, wherein the dicarboxylate ester represented by the general formula (1) is heated and stirred, and γ-butyrolactone and an alkaline metal alcoholate are added to perform the condensation reaction.

In preferred embodiments, R in the general formula (1) is an alkyl group having 1 to 6 carbon atoms, the condensation reaction is performed while removing alcohol by distillation under reduced pressure, and the condensation reaction is performed by varying the reduced pressure by two stages or more.

The alkaline metal salt of the 2-(ω-alkoxycarbonylalkanoyl)-4-butanolide produced by the foregoing step and represented by the general formula (3) and the unreacted dicarboxylate ester are separated from each other and purified. A method in accordance with the present invention for separating and purifying an alkaline metal salt of 2-(ω-alkoxycarbonylalkanoyl)-4-butanolide represented by the general formula (3) and unreacted dicarboxylate ester from a condensation solution of γ-butyrolactone and the dicarboxylate ester represented by the general formula (1) comprises solid-liquid separation using a solvent unreactive to the alkaline metal salt of 2-(ω-alkoxycarbonylalkanoyl)-4-butanolide.

Another method in accordance with the present invention for separating and purifying an alkaline metal salt of 2-(ω-alkoxycarbonylalkanoyl)-4-butanolide represented by the general formula (3), a derivative thereof being an alkaline metal salt of ω-hydroxy-(ω-2)-carboxy-(ω-3)-ketoaliphatic acid represented by the general formula (4), an alkaline metal salt of ω-hydroxy-(ω-3)-ketoaliphatic acid represented by the general formula (5), an alkaline metal salt of ω-hydroxy-(ω-2)-carboxy-(ω-3)-ketoaliphatic acid ester represented by the general formula (6), and an unreacted dicarboxylate ester from a condensation solution of γ-butyrolactone and a dicarboxylate ester represented by the above-mentioned general formula (1) comprises extraction using water or an aqueous alkaline solution:

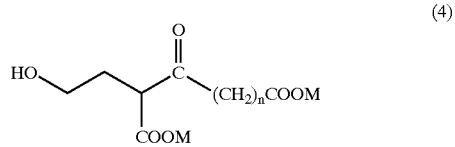
(4)

wherein n is an integer of 7 to 13 and M is an alkaline metal;

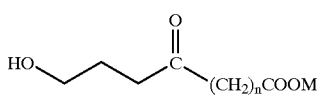
(5)

wherein n is an integer of 7 to 13 and M is an alkaline metal; and

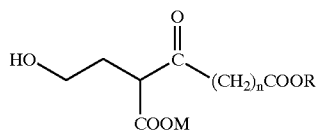
(6)

wherein n is an integer of 7 to 13, R is an alkyl group, and M is an alkaline metal. The compounds represented by the general formulae (3), (4), (5) and (6) may be extracted using an inactive solvent with water or an aqueous alkaline solution.

Also, in the present invention, an ester of ω-hydroxy-(ω-3)-ketoaliphatic acid represented by the general formula (7) is produced:

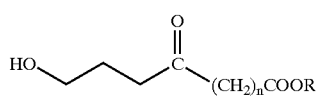
(7)

wherein n is an integer of 7 to 13 and R is an alkyl group.

A method in accordance with the present invention for producing an ester of ω-hydroxy-(ω-3)-ketoaliphatic acid comprises selective hydrolysis and decarboxylation of the γ-butyrolactone portion of an alkaline metal salt of 2-(ω-alkoxycarbonylalkanoyl)-4-butanolide represented by the general formula (3):

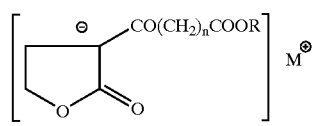
(3)

wherein n is an integer of 7 to 13, R is an alkyl group, and M is an alkaline metal. In the present invention, the ester of ω-hydroxy-(ω-3)-ketoaliphatic acid is obtainable by hydrolysis and decarboxylation of an alkaline metal salt of 2-(ω-alkoxycarbonylalkanoyl)-4-butanolide represented by the general formula (3) in the presence of a weak acid:

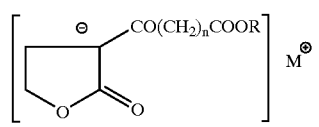
(3)

wherein n is an integer of 7 to 13, R is an alkyl group, and M is an alkaline metal.

The ester of ω-hydroxy-(ω-3)-ketoaliphatic acid represented by the general formula (7) obtained in the present invention is a novel compound:

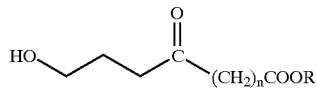
(7)

wherein n is 10 or 11, and R is an alkyl group. R in the general formula (7) is preferably an alkyl group having 1 to 6 carbon atoms.

In the present invention, α,ω-dihydroxy-δ,(ω-3)-alkanedione represented by the general formula (9) is recovered by adding a required amount of alkaline to a mixture containing the compounds represented by the general formulae (3), (4), (5) and (6) separated from the condensation solution for hydrolysis and decarboxylation, and then by extracting the α,ω-dihydroxy-δ,(ω-3)-alkanedione represented by the general formula (9) with an organic solvent from a mixture containing three compounds, an alkaline metal salt of ω-hydroxy-(ω-3)-ketoaliphatic acid represented by the general formula (5), an alkaline metal salt of a long-chain dicarboxylic acid represented by the general formula (8), and the α,ω-dihydroxy-δ,(ω-3)-alkanedione represented by the general formula (9), or by selectively crystallizing the α,ω-dihydroxy-δ,(ω-3)-alkanedione represented by the general formula (9) from the mixture:

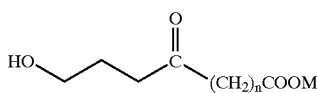
(5)

wherein n is an integer of 7 to 13 and M is an alkaline metal;

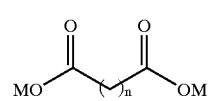
(8)

wherein n is an integer of 7 to 13 and M is an alkaline metal;

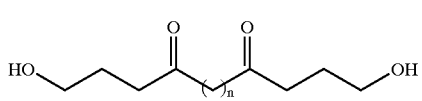
(9)

wherein n is an integer of 7 to 13.

In the present invention, the alkaline metal salt of the ω-hydroxy-(ω-3)-ketoaliphatic acid represented by the general formula (5) is selectively crystallized from the mixture containing the alkaline metal salt of the ω-hydroxy-(ω-3)-ketoaliphatic acid represented by the general formula (5) and the alkaline metal salt of long-chain dicarboxylic acid represented by the general formula (8), and these are separated into a cake and a filtrate by solid-liquid separation to separate and recover the alkaline metal salt of ω-hydroxy-(ω-3)-ketoaliphatic acid represented by the general formula (5) and the alkaline metal salt of long-chain dicarboxylic acid represented by the general formula (8):

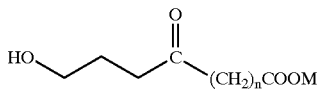
(5)

wherein n is an integer of 7 to 13 and M is an alkaline metal;

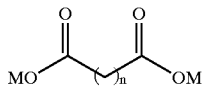
(8)

wherein n is an integer of 7 to 13 and M is an alkaline metal.

Adjusting the pH value of the mixture containing the ω-hydroxy-(ω-3)-ketoaliphatic acid represented by the general formula (5) to 5 to 7 with a mineral acid permits separation and recovery of ω-hydroxy-(ω-3)-ketoaliphatic acid represented by the general formula (10) and the alkaline metal salt of long-chain dicarboxylic acid represented by the general formula (8):

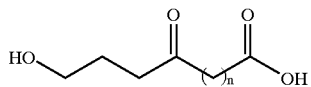
(10)

wherein n is an integer up to 13.

In addition, adjusting the pH value of the filtrate containing the alkaline metal salt of long-chain dicarboxylic acid represented by the general formula (8) to 3 to 5 with a mineral acid permits separation and recovery of a long-chain dicarboxylic acid represented by the general formula (11):

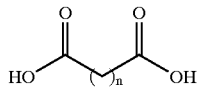
(11)

wherein n is an integer up to 13.

The target of the present invention is also achieved by a combination of these methods.

BEST MODE FOR CARRYING OUT THE INVENTION

In the present invention, γ-butyrolactone is first allowed to react by condensation with a dicarboxylate ester represented by the general formula (1) to form 2-(ω-alkoxycarbonylalkanoyl)-4-butanolide represented by the general formula (2) or an alkaline metal salt of 2-(ω-alkoxycarbonylalkanoyl)-4-butanolide represented by the general formula (3):

ROOC(CH$_2$)nCOOR (1)

wherein n is an integer of 7 to 13 and R is an alkyl group;

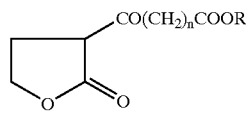
(2)

wherein n is an integer of 7 to 13 and R is an alkyl group;

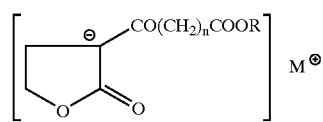
(3)

wherein n is an integer of 7 to 13, R is an alkyl group, and M is an alkaline metal.

The condensation reaction of dicarboxylate ester and γ-butyrolactone in the presence of a basic condensation agent is complicated; hence, it is presumed that the selectivity and yield greatly depend on the reaction process, such as the method for feeding raw materials and the method for removing methanol formed. As a result of intensive research by the present inventors on the point aimed at the reaction mechanism regarding the formation of alcohol, it was discovered that 2-(ω-alkoxycarbonylalkanoyl)-4-butanolide and its alkaline metal salt are obtained with satisfactory selectivity and yield, as will be described below.

In the first stage, γ-butyrolactone and an alkaline metal alcoholate are added as droplets to a hot dicarboxylate ester while stirring under reduced pressure which is sufficient to evaporate a formed alcohol to allow the reaction to proceed while distilling the alcohol from the system. In the second stage, heating with stirring is continued under a further reduced pressure to allow the reaction to proceed while distilling the alcohol from the system. It was discovered that 2-(ω-alkoxycarbonylalkanoyl)-4-butanolide and its alkaline metal salt are obtained with satisfactory selectivity and yield by such stages.

Accordingly, a characteristic feature of the present invention is addition of γ-butyrolactone and an alkaline metal alcoholate to a hot dicarboxylate ester while stirring to allow condensation reaction. In this case, the γ-butyrolactone and the alkaline metal alcoholate may be added as a mixture or independently.

It is preferable that the reaction be performed while distilling alcohol from the system. In addition, it is preferable in view of further satisfactory selectivity and yield that the reaction be continued while distilling the residual alcohol from the system under further reduced pressure.

R in the dicarboxylate ester represented by dicarboxylate ester represented by the general formula (1), ROOC(CH$_2$)nCOOR wherein n is an integer of 7 to 13 and R is an alkyl group, is preferably an alkyl group having 1 to 6 carbon atoms, in view of convenience of use.

Examples of R include methyl, ethyl, propyl, butyl, isobutyl, pentyl, and hexyl groups. Among these, methyl is preferable.

Examples of preferable dicarboxylate esters represented by the general formula (1) include dimethyl 1,12-dodecanedicarboxylate and dimethyl 1,13-tridecanedicarboxylate (dimethyl brassylate).

In the present invention, the condensation reaction proceeds in the presence of an alkaline metal alcoholate. Preferable alkaline metal alcoholates are represented by the general formula R'OM wherein R' is an alkyl group having 1 to 4 carbon atoms and M is an alkaline metal.

Examples of the alkaline metal alcoholates include sodium methylate, sodium ethylate, sodium propylate, sodium butylate, potassium methylate, potassium ethylate, potassium propylate, and potassium butylate.

Although the amount of the alkaline metal alcoholate used in the present invention is not limited, the amount is preferably 0.1 to 5 equivalents and more preferably 0.5 to 3 equivalents with respect to γ-butyrolactone. When the amount of alkaline metal alcoholate used is small, the yield will decrease. When the amount used is higher than the predetermined level, the selectivity may decrease.

It is preferable in the present invention that the dicarboxylate ester represented by the general formula (1) be used in an excess amount on a molar basis to γ-butyrolactone, and particularly 2 times or more by mole. The use of the dicarboxylate ester in an amount of 2 times or more by mole results in a particular improvement in selectivity.

If unreacted dicarboxylate ester is present when the present invention is executed, it is preferable in view of effective reaction that the unreacted dicarboxylate ester be recovered from the reaction mixture to recycle it to the condensation reaction. In the present invention, the unreacted dicarboxylate ester can be readily recovered from the reaction mixture by extraction with water or an aqueous alkaline solution or by solid-liquid separation; hence a combination of the excessive use and recycling use of the dicarboxylate ester permits more effective reaction.

The condensation reaction in the present invention is preferably performed under reduced pressure to effectively remove alcohol. A preferable reduced pressure is in a range of 50 to 760 mmHg, and more preferably 100 to 600 mmHg. The pressure may be diminished by two or more stages. For example, the pressure during the reaction is diminished to approximately 500 to 700 mmHg which is sufficient for distillation of alcohol in the first stage, and then further diminished to approximately 50 to 300 mmHg in the second stage.

Although the heating temperature in the condensation reaction is not limited, a preferable condition is set in relation to the reduced pressure. A preferable temperature lies in a range of 30 to 200° C., and more preferably 50 to 150° C.

Although no solvent is required in the present invention, a solvent used in general ester condensation may be used in this reaction as long as it does not decrease the activity of the alkaline metal alcoholate.

The reaction in accordance with the present invention may be performed by a batch system, a continuous system, or a multistage system.

The alkaline metal salt of 2-(ω-alkoxycarbonylalkanoyl)-4-butanolide obtained in the present invention can be readily converted with high yield into ω-hydroxyaliphatic acid, which is an important intermediate for a large cyclic lactone-based perfume, as will be described later.

The product of the condensation reaction of the dicarboxylate ester represented by the general formula (1) with γ-butyrolactone is a β-ketoester type compound which is generally present as an alkaline salt represented by the general formula (3) in the reaction solution:

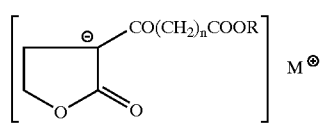

(3)

wherein n is an integer of 7 to 13, R is an alkyl group, and M is an alkaline metal. It was discovered that the alkaline metal salt represented by the general formula (3) has significantly lower solubility in an organic solvent such as n-hexane. The salt is readily soluble in an aqueous alkaline solution. The γ-butyrolactone portion and the ester terminal are rapidly hydrolyzed to form an alkaline metal salt of dicarboxylic acid represented by the general formula (4), and the salt is partly decarboxylated to form an alkaline metal salt represented by the general formula (5) when a certain amount of alkaline metal hydroxide is added:

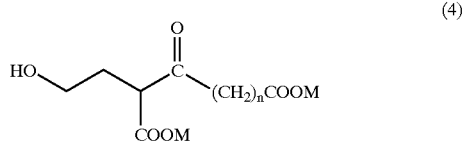

(4)

wherein n is an integer of 7 to 13 and M is an alkaline metal;

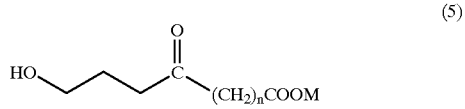

(5)

In contrast, the dicarboxylate ester represented by the general formula (1) used in excess in the condensation reaction of the present invention remains without reaction in the solution. The compound is significantly soluble in an organic solvent such as n-hexane.

Accordingly, the present inventors have intensively studied solubility of the alkaline metal salt of 2-(ω-alkoxycarbonylalkanoyl)-4-butanolide in organic solvents and water, have discovered a purification method for independently recovering the alkaline metal salt of 2-(ω-alkoxycarbonylalkanoyl)-4-butanolide with its derivative, and the unreacted dicarboxylate ester with ease and high yield, and have completed the present invention.

The method in the present invention separates the alkaline metal salt represented by the general formula (3) and the unreacted dicarboxylate ester represented by the general formula (1) by solid-liquid separation such as filtration (hereinafter referred to as a solid-liquid separation method).

An organic solvent, which can dissolve the unreacted dicarboxylate ester and is unreactive to the alkali and the alkaline metal salt of 2-(ω-alkoxycarbonylalkanoyl)-4-butanolide, is added to the condensation solution to sufficiently dissolve the unreacted dicarboxylate ester and to form a salt suspension. The suspension is separated into a liquid component and a solid component by any known method such as filtration or centrifugal separation. The solid component is thoroughly washed with the solvent to remove the unreacted dicarboxylate ester. The liquid component and the washings are concentrated together and recycled to the next condensation reaction.

On the other hand, the solid component can be used without further treatment or after converting it into 2-(ω-alkoxycarbonylalkanoyl)-4-butanolide by acidification. It can also be used for hydrolysis and decarboxylation in an aqueous alkaline solution.

The present invention also relates to a method for extracting the salt of 2-(ω-alkoxycarbonylalkanoyl)-4-butanolide with water and the unreacted dicarboxylate ester with an organic solvent for separation thereof (hereinafter referred to as an alkaline extraction method).

Water or an aqueous alkaline solution is added to the condensation solution to dissolve the alkaline metal salt of 2-(ω-alkoxycarbonylalkanoyl)-4-butanolide, the unreacted dicarboxylate ester is recovered into an organic layer from the mixture by a separative operation, and then washed with water to recycle it for the next condensation reaction.

On the other hand, the aqueous layer contains the alkaline metal salt represented by the general formula (3), the compound represented by the general formula (6), the alkaline metal salt represented by the general formula (4) in the case of addition of a given amount of alkaline metal hydroxide, and the alkaline metal slat represented by the general formula (5) formed by partial decarboxylation in the case of addition of a given amount of alkaline metal hydroxide. This phenomenon was clarified by determining the composition of the crystal extract after acidification of the aqueous layer obtained by the above-mentioned operation.

It was found that the crystal extract primarily contains the compound represented by the general formula (2), long-chain dicarboxylic acid, 2-(ω-carboxyundecanoyl)-4-butanolide represented by the general formula (12), and ω-hydroxy-(ω-3)-ketoaliphatic acid represented by the general formula (10):

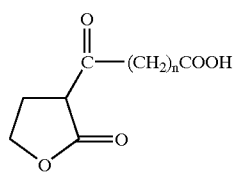
(12)

wherein n is an integer of 7 to 13;

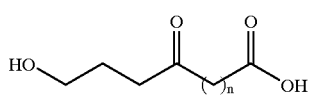
(10)

wherein n is an integer of 7 to 13.

It is presumed in the present invention that the crystal extract contains the 2-(ω-alkoxycarbonylalkanoyl)-4-butanolide represented by the general formula (2) and the 2-(ω-carboxyundecanoyl)-4-butanolide represented by the general formula (12) for the following reason. When the alkaline metal salt represented by the general formula (3) is dissolved in an aqueous alkaline solution, the γ-butyrolactone portion is rapidly hydrolyzed to form the compound represented by the general formula (6).

Acidification of the extract forms a compound represented by the general formula (13):

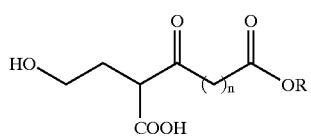
(13)

wherein n is an integer of 7 to 13. The product is rapidly dehydrated to form a lactone ring and thus the compound represented by the general formula (2). When a given amount of alkaline is added, the terminal ester group in the general formula (6) is also presumably hydrolyzed to form the alkaline metal salt of dicarboxylic acid represented by the general formula (4).

Acidification of the compound represented by the general formula (4) forms a dicarboxylic acid represented by the general formula (14):

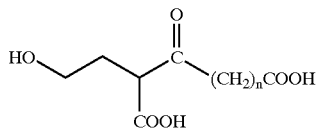
(14)

wherein n is an integer of 7 to 13. The product is rapidly dehydrated to form a lactone ring and thus 2-(ω-carboxyundecanoyl)-4-butanolide represented by the general formula (12).

The formation of ω-hydroxy-(ω-3)-ketoaliphatic acid is caused by decarboxylation of the β-ketoacid occurring when the amount of the alkaline metal salt is in excess with respect to hydrolysis.

The resulting aqueous layer can be used for the subsequent hydrolysis and decarboxylation.

Solvents used in the present invention are not limited as long as they are unreactive to the alkali and the salt of 2-(ω-alkoxycarbonylalkanoyl)-4-butanolide. Examples of such solvents include organic solvents, such as pentane, hexane, heptane, octane, cyclohexane, benzene, toluene, xylene, diethylether, and isopropyl ether.

Although the alkaline extraction method can be achieved without using a solvent, the use of a solvent is preferable. The amount of the solvent is preferably 0 to 10 times by weight, and more preferably 0.5 to 5 times by weight with respect to the condensation solution. The temperature of dissolution into the solvent and the temperature of the alkaline extraction are not limited within a range not causing solidification of the organic solvent, and lie in a range of generally 0° C. to 100° C., and preferably 20° C. to 50° C.

The alkaline compounds used in the alkaline extraction in the present invention are not limited as long as they can extract 2-(ω-alkoxycarbonylalkanoyl)-4-butanolide and its alkaline metal salt and derivative. Examples of usable alkaline compounds include alkaline metal hydroxide, such as lithium hydroxide, sodium hydroxide, and potassium hydroxide; alkaline metal carbonates, such as sodium carbonate and potassium carbonate; and alkaline earth metal hydroxides, such as barium hydroxide.

The concentration of the aqueous alkaline solution is not limited, and lies in a range of preferably 0.5 to 50%, and more preferably 1 to 15%. In addition, the amount is not limited, and lies in a range of preferably 0.1 to 10 times by weight and more preferably 0.5 to 2 times by weight with respect to the condensation solution. The purification in accordance with the present invention can be performed by either a batch system or a continuous system.

Furthermore, the present inventors have discovered that heating of the alkaline metal salt of 2-(ω-alkoxycarbonylalkanoyl)-4-butanolide obtained in the above-described operation with a weak acid such as phosphoric acid forms the ester of ω-hydroxy-(ω-3)-ketoaliphatic acid represented by the general formula (7) with high yield:

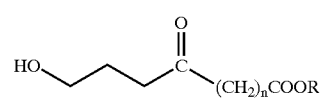
(7)

wherein n is an integer of 7 to 13 and R is an alkyl group. The present inventors have also discovered that the compound represented by the general formula (7) is oil-soluble and thus can be readily separable from the reaction solution, and have completed the present invention. The ester of ω-hydroxyketoaliphatic acid is useful as an intermediate in the production of ω-hydroxyaliphatic acid which is an important intermediate for a macro cyclic lactone-based perfume in the perfume industry.

Among the esters of ω-hydroxy-(ω-3)-ketoaliphatic acid represented by the general formula (7), novel compounds are esters of ω-hydroxy-(ω-3)-ketoaliphatic acid wherein n is 10 or 11.

In the present invention, selective hydrolysis and decarboxylation of the γ-butyrolactone portion in the alkaline metal salt of 2-(ω-alkoxycarbonylalkanoyl)-4-butanolide obtained in the above-mentioned operation forms the ester of ω-hydroxy-(ω-3)-ketoaliphatic acid represented by the general formula (7):

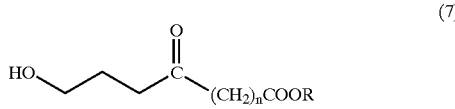

(7)

wherein n is an integer of 7 to 13 and R is an alkyl group. In addition, in the present invention, hydrolysis and decarboxylation of the alkaline metal salt of 2-(ω-alkoxycarbonylalkanoyl)-4-butanolide represented by the general formula (3) by heating with a weak acid forms the ester of ω-hydroxy-(ω-3)-ketoaliphatic acid represented by the general formula (7).

Types of the weak acids used in hydrolysis and decarboxylation in the present invention are not limited. Examples of weak acids include phosphoric acid, pyrophosphoric acid, and carbonic acid. Sodium dihydrogenphosphate and the like are also usable. The amount of the weak acid used is not limited, and lies in a range of 0.5 to 3 equivalents, and more preferably 0.5 to 1 equivalents with respect to 1 mole of alkaline metal salt of 2-(ω-alkoxycarbonylalkanoyl)-4-butanolide.

The amount of water used in the reaction in the present invention is not limited, and preferably lies in a range of 2 to 20 times with respect to the alkaline metal salt of 2-(ω-alkoxycarbonylalkanoyl)-4-butanolide.

A water-soluble organic solvent may or may not be used in the hydrolysis and decarboxylation in the present invention. Examples of the water-soluble organic solvents include methanol, ethanol, diethylene glycol, triethylene glycol, dioxane, tetrahydrofuran, and 1,2-dimethoxyethane. The water-soluble organic solvent is preferably used in an amount of 0.05 to 3 parts by weight to 1 parts by weight of water.

The reaction in accordance with the present invention requires heating. The heating is performed in the presence of a weak acid such as phosphoric acid in the present invention. The heating temperature preferably lies in a range of 80 to 110° C. The reaction time is appropriately determined depending on the reaction temperature and fed raw materials, and generally lies in a range of 1 to 20 hours. The reaction can be performed by a batch system or a continuous system. Isolation and purification of the reaction products can be achieved by any conventional unit operations including liquid separation, extraction, washing and recrystallization.

The ester of ω-hydroxy-(ω-3)-ketoaliphatic acid represented by the general formula (7) obtained in the present invention can be easily converted into ω-hydroxy-aliphatic acid as an important intermediate for a macro cyclic lactone-based perfume with high yield and industrial advantages.

The —COOR group of the ester of ω-hydroxy-(ω-3)-ketoaliphatic acid is hydrolyzed to form the alkaline metal salt of ω-hydroxy-(ω-3)-ketoaliphatic acid represented by the general formula (5) by heating in an aqueous alkaline metal hydroxide solution or a mixed solvent of a water-soluble organic solvent and water. The —CO— group is reduced to —CH$_2$— group by the conventional Wolff-Kishner ketone reduction process, and thus yields ω-hydroxyaliphatic acid. As described above, the ester of ω-hydroxyaliphatic acid is useful as a raw synthetic material and as an intermediate, and particularly as an intermediate in the production of ω-hydroxyaliphatic acid which is an important intermediate for large cyclic lactone-based perfumes, such as cyclopentadecanolide and cyclohexadecanolide, in the perfume industry.

The present invention relates to separation of the compound represented by the general formula (9) by extraction with an organic solvent or crystallization, in which the compound is formed by hydrolysis and decarboxylation of the byproduct in the condensation reaction which is present in the reaction mixture after extraction, hydrolysis, and decarboxylation under a basic condition of the condensation products of the above-mentioned dicarboxylate ester and γ-butyrolactone:

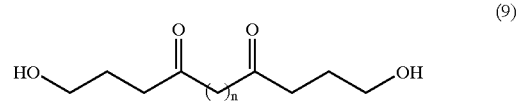

(9)

wherein n is an integer of 7 to 13. The residual aqueous solution is treated at a predetermined temperature to selectively crystallize the alkaline metal salt of ω-hydroxy-(ω-3)-ketoaliphatic acid, and then subjected to solid-liquid separation to separate the solution into the cake and the filtrate. The alkaline metal salt of ω-hydroxy-(ω-3)-ketoaliphatic acid represented by the general formula (5) and the alkaline metal salt of dicarboxylic acid represented by the general formula (8) are thereby separately recovered. Alternatively, the resulting cake and filtrate are independently treated with a mineral acid to separately recover the ω-hydroxy-(ω-3)-ketoaliphatic acid represented by the general formula (10) and the dicarboxylic acid represented by the general formula (11):

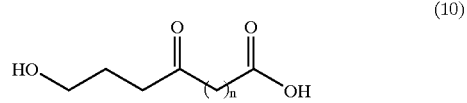

(10)

wherein n is an integer of 7 to 13;

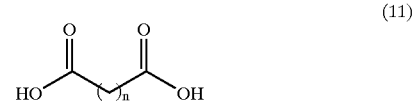

(11)

wherein n is an integer of 7 to 13.

Alternatively, the pH of the mixture containing the alkaline metal salt of ω-hydroxy-(ω-3)-ketoaliphatic acid represented by the general formula (5) and the alkaline metal salt of long-chain dicarboxylic acid represented by the general formula (8) is adjusted to 5 to 7 with a mineral acid to precipitate the compound represented by the general formula (10), and is then subjected to solid-liquid separation to separately recover the ω-hydroxy-(ω-3)-ketoaliphatic acid represented by the general formula (10) and the alkaline metal salt of long-chain dicarboxylic acid represented by the general formula (8). The pH of the filtrate is adjusted to 3 to 5, if necessary, to recover the long-chain dicarboxylic acid represented by the general formula (11) by precipitation and then solid-liquid separation.

For example, the compound represented by the general formula (9) is removed by extraction from, or selectively crystallized by treatment at a predetermined temperature from, the mixture containing the alkaline metal salt of ω-hydroxy-(ω-3)-ketoaliphatic acid represented by the general formula (5), the alkaline metal salt of long-chain dicarboxylic acid represented by the general formula (8), and the α,ω-dihydroxy-δ,(ω-3)-alkanedione represented by the general formula (9). Next, the aqueous solution after removing the cake by solid-liquid separation is treated at a predetermined temperature to selectively crystallize the compound represented by the general formula (5) and then separated into a cake and a filtrate by solid-liquid separation. When the filtrate contains a small amount of compound represented by the general formula (5), the pH of the filtrate is adjusted to 5 to 7 to crystallize the compound represented by the general formula (10) and to separately recover the ω-hydroxy-(ω-3)-ketoaliphatic acid represented by the general formula (10) and the alkaline metal salt of long-chain dicarboxylic acid represented by the general formula (8) after the subsequent solid-liquid separation. The pH of the resulting filtrate is adjusted to 3 to 5 to crystallize the compound represented by the general formula (11) and to separately recover the alkaline metal salt of long-chain dicarboxylic acid represented by the general formula (8) after the subsequent solid-liquid separation.

Any organic solvent which is unreactive in basic conditions and insoluble in water can be used without limitation to separate the α,ω-dihydroxy-δ,(ω-3)-alkanedione represented by the general formula (9) from the reaction mixture. Examples of the organic solvents include benzene, toluene, xylene, tetralin, decalin, pentane, hexane, heptane, octane, cyclohexane, isopropyl ether, and dibutyl ether. Among them, toluene is preferably used.

The amount of the organic solvent used in the present invention is not limited, and lies in a range of preferably 0.5 to 20 parts by weight, and more preferably 1 to 10 parts by weight with respect to the reaction mixture in view of processing and material cost.

The extraction temperature of the compound represented by the general formula (9) is not limited in the present invention, and lies in a range of 50 to 110° C., and preferably 60 to 90° C. in view of the boiling points of the organic solvent and water used for the extraction; however, the higher the extraction temperature, the higher the extraction efficiency. Although the organic layer may contain the compound represented by the general formula (5), the compound can be substantially recovered by reverse extraction with hot water.

Although the crystallization temperature of the compound represented by the general formula (9) in the present invention significantly depends on the composition of the reaction mixture and particularly the water content, it is not limited as long as the compound represented by the general formula (9) is crystallized and the salts represented by the general formulae (5) and (8) are dissolved. The crystallization temperature is preferably in a range of −20 to 80° C., and more preferably 0 to 40° C., in view of processing.

In the crystallization of the compound represented by the general formula (9), although the water content in the reaction mixture is significantly affected by the composition and temperature of the reaction mixture, it is not limited as long as the water content permits crystallyzation of the compound represented by the general formula (9) and dissolution of the salts represented by the general formulae (5) and (8). The water content is preferably in a range of 50 to 99 percent by weight, and more preferably 70 to 90 percent by weight in view of processing.

Solid-liquid separation of the crystal represented by the general formula (9) in the present invention may be performed by any conventional method such as centrifugal sedimentation, centrifugal hydroextraction, or filtration. Although the resulting cake may contain the salts represented by the general formulae (5) and (8) in some cases, washing with water enables an increase in purity of the compound represented by the general formula (9) in the cake and recovery of the salts represented by the general formulae (5) and (8) as an aqueous solution.

The extraction step in the present invention may be of a batch type or a multi-vessel type, or a continuous type.

The crystallization conditions of the alkaline metal salt of ω-hydroxy-(ω-3)-ketoaliphatic acid represented by the general formula (5) will now be described.

Although the crystallization temperature of the compound represented by the general formula (5) significantly depends on the composition and particularly on the water content of the reaction mixture, it is not limited as long as the crystals of the compound represented by the general formula (5) forms and the compound represented by the general formula (2) is dissolved. The crystallization temperature is in a range of preferably −20 to 80° C., and more preferably 0 to 40° C. in view of processing.

Although the water content in the present invention significantly depends on the composition and temperature of the reaction mixture, it is not limited as long as the crystals of the compound represented by the general formula (5) forms and the compound represented by the general formula (8) is dissolved. The water content is in a range of preferably 50 to 99 percent by weight, and more preferably 70 to 90 percent by weight in view of processing.

The solid-liquid separation of the crystal formed in the present invention can be performed by any conventional method, such as centrifugal sedimentation, centrifugal hydroextraction, or filtration. Although the resulting cake may contain the compound represented by the general formula (8) in some cases, washing with water enables an increase in purity of the compound represented by the general formula (5) in the cake and recovery of the compound represented by the general formula (8) as an aqueous solution.

The cake obtained in the production of the large cyclic lactone can be used in the next reductive reaction without further treatment or after acidification. The reductive reaction can be achieved by a conventional method, such as Wolff-Kishner reduction, or Clemmensen reduction.

The mineral acid used for acidifying the alkaline metal salts represented by the general formulae (5) and (8) is not limited, and sulfuric acid and hydrochloric acid are often used. The aliphatic acid after the acidification can be recovered by a solid-liquid separation method, such as centrifugal sedimentation, centrifugal hydroextraction, or filtration; or extraction with an organic solvent, such as benzene, toluene, xylene, pentane, hexane, heptane, octane, cyclohexane, diethyl ether, isopropyl ether, ethyl acetate, dichloromethane, chloroform, carbon tetrachloride, or dichloroethane, although the method depends on the shape of the aliphatic acid.

When the compound represented by the general formula (10) is obtained from the mixture of the compounds represented by the general formulae (5) and (8) with a mineral acid, the pH is preferably in a range of 5 to 7, and more preferably 5.5 to 6.5. When the compound represented by the general formula (11) is obtained after acidification of the compound represented by the general formula (8), the pH is preferably in a range of 3 to 4, and more preferably 3.5 to 4.5. A further reduction in the pH value is not preferable due to an increased amount of mineral acid used and increased material cost, although the recovery rate and purity of the compound represented by the general formula (11) are not affected.

EXAMPLES

The present invention will now be described in more detail with reference to the following EXAMPLES. These EXAMPLES are for exemplification and should not in any way be construed as limitative.

Example 1

Dimethyl 1,12-dodecanedioate (105.00 g, 406.4 mmol) was fed into a reaction vessel and was heated to 105° C. while being stirred under a reduced pressure of 600 mm Hg. A mixture of γ-butyrolactone (8.75 g, 101.6 mmol) and a 28-wt % sodium methoxide in methanol solution (19.60 g, 101.6 mmol), which were mixed at room temperature, was added dropwise to the heated dimethyl 1,12-dodecanedioate over a period of 30 minutes while removing methanol by distillation. After the reaction had proceeded for 30 minutes, the mixture was evacuated to 200 mmHg to continue the reaction for further 120 minutes.

The mixture was subjected to normal pressure, cooled, poured into a diluted hydrochloric acid solution, and then extracted with ethyl acetate. The organic layer was washed with water, dried with anhydrous magnesium sulfate, and was distilled to remove the solvent. The oily residue was distilled under a reduced pressure (bath temperature: 170 to 180° C./0.5 to 0.2 mmHg) to remove the excess dimethyl 1,12-dodecanedioate. The resulting products were 81.9 g of the distilled component and 25.1 g of the distillation residue.

According to the results of gas chromatography, the distillation residue contains 88.6 percent by weight of the compound represented by the general formula (2) (n=10, R=Me). The yield was 80.2% and the selectivity was 83.2%.

Example 2

Dimethyl 1,12-dodecanedioate (105.00 g, 406.4 mmol) was fed into a reaction vessel and was heated to 105° C. while being stirred under a reduced pressure of 600 mm Hg. A mixture of γ-butyrolactone (8.75 g, 101.6 mmol) and a 28-wt % sodium methoxide in methanol solution (19.60 g, 101.6 mmol), which were mixed at room temperature, was added dropwise to the heated dimethyl 1,12-dodecanedioate over a period of 30 minutes while removing methanol by distillation. After the reaction had proceeded for 30 minutes, the mixture was evacuated to 200 mmHg to continue the reaction for further 240 minutes.

The mixture was subjected to normal pressure, cooled, poured into a diluted hydrochloric acid solution, and then extracted with ethyl acetate. The organic layer was washed with water, dried with anhydrous magnesium sulfate, and was evaporated to remove the solvent. The oily residue was distilled under a reduced pressure (bath temperature: 170 to 180° C./0.5 to 0.2 mmHg) to remove the excess dimethyl 1,12-dodecanedioate. The resulting products were 82.2 g of the distilled component and 26.5 g of the distillation residue. It was found that the distillation residue contains 88.1 percent by weight of the compound represented by the general formula (2) (n=10, R=Me). The yield was 81.4% and the selectivity was 87.9%.

Example 3

Dimethyl 1,12-dodecanedioate (105.00 g, 406.4 mmol) was fed into a reaction vessel and was heated to 105° C. while being stirred under a reduced pressure of 500 mm Hg. A mixture of γ-butyrolactone (8.75 g, 101.6 mmol) and a 28-wt % sodium methoxide in methanol solution (19.60 g, 101.6 mmol), which were mixed at room temperature, was added dropwise to the heated dimethyl 1,12-dodecanedioate over a period of 30 minutes while removing methanol by distillation. After the reaction had proceeded for 30 minutes, the mixture was evacuated to 100 mmHg to continue the reaction for further 120 minutes.

The mixture was subjected to normal pressure, cooled, poured into a diluted hydrochloric acid solution, and then extracted with ethyl acetate. The organic layer was washed with water, dried with anhydrous magnesium sulfate, and was distilled to remove the solvent. The oily residue was distilled under a reduced pressure (bath temperature: 170 to 180° C./0.5 to 0.2 mmHg) to remove the excess dimethyl 1,12-dodecanedioate. The resulting products were 81.4 g of the distilled component and 27.2 g of the distillation residue. It was found that the distillation residue contains 88.3 percent by weight of the compound represented by the general formula (2) (n=10, R=Me). The yield was 81.6% and the selectivity was 86.0%.

Comparative Example 1

Dimethyl 1,12-dodecanedioate (105.00 g, 406.4 mmol), γ-butyrolactone (8.75 g, 101.6 mmol), and a 28-wt % sodium methoxide in methanol solution (19.60 g, 101.6 mmol) were mixed at 50° C., and then heated to 110° C. over a period of 45 minutes while removing methanol by distillation. After the reaction had proceeded for 30 minutes, the mixture was evacuated to 630 mmHg to continue the reaction for further 30 minutes.

The mixture was subjected to normal pressure, cooled, poured into a diluted hydrochloric acid solution, and then extracted with ethyl acetate. The organic layer was washed with water, dried with anhydrous magnesium sulfate, and was distilled to remove the solvent. The oily residue was distilled under a reduced pressure (bath temperature: 170 to 180° C./0.5 to 0.2 mmHg) to remove the excess dimethyl 1,12-dodecanedioate. The resulting products were 81.5 g of the distilled component and 25.6 g of the distillation residue. It was found that the distillation residue contains 85.1 percent by weight of the compound represented by the general formula (1) (n=10, R=Me). The yield was 79.0% and the selectivity was 79.0%.

Example 4

Solid-liquid Separation Method 116.2 g of a condensation solution (confirmed by quantitative analysis, after acidification of a part, that the solution contains 25.71 g of the condensation product and 80.70 g of the unreacted ester) prepared from dimethyl 1,12-dodecanedioate (105.00 g, 406.4 mmol), γ-butyrolactone (8.75 g, 101.6 mmol), and a 28-wt % sodium methoxide in methanol solution (19.60 g, 101.6 mmol) was heated to 50° C. while being stirred. Into the solution, 565 g of n-hexane was added, and cooled to 20° C. while being stirred to form a suspension containing a pale yellow precipitate and a clear supernatant liquid. The suspension was separated into a precipitate and a supernatant liquid using a pressure filter. The cake was thoroughly washed with n-hexane.

The filtrate and the washings were mixed and then n-hexane was removed by distillation to obtain 80.94 of concentrate. According to the gas chromatographic quantitative analysis of the concentrate, it contained 99.2% of the compound represented by the general formula (1) (n=10, R=Me). The yield was 99.5%.

After acidifying 1.00 g among 35.35 g of the resulting cake, it was extracted with ethyl acetate. The organic layer was washed with water, dried with anhydrous sodium sulfate, and was distilled to remove the solvent. A crystal product in an amount of 0.92 g was thereby obtained. According to gas chromatographic determination, the crystal product contains 0.73 g of compound represented by the general formula (2) (n=10, R=Me) and 0.01 g of compound represented by the general formula (1) (n=10, R=Me). The recovery of the compound represented by the general formula (2) was 100 percent by weight, and the residual rate of the ester of dicarboxylic acid represented by the general formula (1) was 0.4 percent by weight.

Example 5

A condensation solution (confirmed by quantitative analysis, after acidification of a part, that the solution contains 12.25 g of the condensation product and 42.61 g of the unreacted ester) prepared from dimethyl 1,12-dodecanedioate (64.73 g, 207.2 mmol), γ-butyrolactone (4.46 g, 51.8 mmol), and a 28-wt % sodium methoxide in methanol solution (9.99 g, 51.8 mmol) was heated to 50° C. while being stirred. Into the solution, 50.0 g of n-hexane was added, and the solution was stirred for 2 minutes. Next, 50.0 g of water was added while continuing stirring for 30 minutes. The organic layer was washed with water and concentrated. As a result, 44.31 g of a crystalline product containing 94.1% of compound represented by the general formula (1) (n=10, R=Me) was obtained. The recovery was 97.9%.

The aqueous layer was immediately poured into diluted sulfuric acid to acidify the layer, and was extracted with ethyl acetate, followed by washing with water. The solution was dried with anhydrous sodium sulfate and then the solvent was removed by distillation. According to gas chromatographic determination, 13.11 g of the resulting crystal contains 71% of the compound represented by the general formula (2) (n=10, R=Me). The recovery was 78.2%.

Example 6

Alkaline Extraction Method

A condensation solution (confirmed by quantitative analysis, after acidification of a part, that the solution contains 25.49 g of the condensation product and 80.82 g of the unreacted ester) prepared from dimethyl 1,12-dodecanedioate (105.00 g, 406.4 mmol), γ-butyrolactone (8.75 g, 101.6 mmol), and a 28-wt % sodium methoxide in methanol solution (19.60 g, 101.6 mmol) was heated to 50° C. while being stirred. Into the solution, 104.4 g of n-hexane was added, and the solution was stirred for 2 minutes. Next, 107.5 g of an aqueous 5%-KOH solution was added while continuing stirring for 120 minutes. After allowing it to stand for 5 minutes, the mixture was separated into an organic layer and an aqueous layer. The organic layer was washed with water and concentrated. As a result, 80.9 g of a crystalline product containing 98.8% (observed value) of a compound represented by the general formula (1) (n=10, R=Me) was obtained. The recovery was 98.9%.

The aqueous layer was immediately poured into diluted sulfuric acid to acidify the layer, and was extracted with ethyl acetate, followed by washing with water. The solution was dried with anhydrous sodium sulfate, and then the solvent was removed by distillation. According to gas chromatographic determination, the resulting crystal contains 23.1% of the compound represented by the general formula (10) (n=10). A colorless crystal (0.61 g) prepared by silicagel chromatographic fractionation of 1.00 g of the crystal was identified by IR and NMR, and a compound represented by the general formula (12) (n=10) was confirmed.

Example 7

Alkaline Extraction Method

A condensation solution (confirmed by quantitative analysis, after acidification of a part, that the solution contains 25.58 g of the condensation product and 80.56 g of the unreacted ester) prepared from dimethyl 1,12-dodecanedioate (105.00 g, 406.4 mmol), γ-butyrolactone (8.75 g, 101.6 mmol), and a 28-wt % sodium methoxide in methanol solution (19.60 g, 101.6 mmol) was heated to 50° C. while being stirred. Into the solution, 139.7 g of cyclohexane was added, and the solution was stirred for 2 minutes. Next, 143.9 g of an aqueous 5%-KOH solution was added while continuing stirring for 10 minutes. After allowing it to stand for 5 minutes, the mixture was separated into an organic layer and an aqueous layer. The organic layer was washed with water and concentrated. As a result, 81.62 g of a crystalline product containing 98.9% (observed value) of a compound represented by the general formula (1) (n=10, R=Me) was obtained. The recovery was 100.0%.

Reference Example 1

Into the aqueous layer obtained in EXAMPLE 3, 23.3 g of an aqueous 49%-KOH solution was added followed by reflux for 2 hours. After acidification with diluted sulfuric acid, the solution was extracted with ethyl acetate. The organic layer was washed with water and dried with anhydrous sodium sulfate, and then the solvent was removed by distillation to obtain 27.50 g of crude crystal. According to gas chromatographic determination, the crystal contains 80.2 percent by weight of a compound represented by the general formula (10) (n=10). The yield of the compound represented by the general formula (2) (n=10, R=Me) from the condensation solution was 99.0%.

Comparative Example 2

A condensation solution (confirmed by quantitative analysis, after acidification of a part, that the solution contains 25.68 g of the condensation product and 80.67 g of the unreacted ester) prepared from dimethyl 1,12-dodecanedioate (105.00 g, 406.4 mmol), γ-butyrolactone (8.75 g, 101.6 mmol), and a 28-wt % sodium methoxide in methanol solution (19.60 g, 101.6 mmol) was extracted with ethyl acetate after pouring into diluted hydrochloric acid. The organic layer was washed with water and dried with anhydrous magnesium sulfate, and then the solvent was removed by distillation. The resulting oily residue was distilled under reduced pressure (bath temperature: 170 to 180° C./0.5 to 0.2 mmHg) to remove the excess dimethyl 1,2-dodecanedioate. As a result, 802 g of an evacuated component and 31.55 g of the residue were obtained. According to gas chromatographic determination, the evacuated component contains 98.3% of a compound represented by the general formula (1) (n=10, R=Me). The yield was 98%.

The distillation residue (2.00 g) was acidified followed by extraction with ethyl acetate. The organic layer was washed with water and dried with anhydrous sodium sulfate, and then the solvent was removed by distillation. A crystal product in an amount of 1.88 g was obtained. According to gas chromatographic determination, the crystal product contains 84.0 percent by weight of a compound represented by the general formula (5) (n=10, R=Me). The purified yield was 97.00%.

Next, 2.00 g of the distillation residue, sodium hydroxide (1.75 g, 13.7 mmol), 40 g of water, and 20 g of methanol were mixed and fluxed while being heated for 4 hours. After cooling and acidifying, the mixture was extracted with ethyl acetate. The organic layer was washed with water and dried with anhydrous sodium sulfate, and the solvent was distilled. As a result, 1.57 g of a crude crystal product was obtained. According to gas chromatographic determination, the product contains 86.6 percent by weight of a compound represented by the general formula (10) (n=10). The yield was 95 mol percent with regard to the compound represented by the general formula (2).

Example 8

A condensation solution in an amount of 113.2 g (confirmed by quantitative analysis, after acidification of a part, that the solution contains 25.65 g of the condensation product and 80.84 g of the unreacted ester) prepared from dimethyl 1,12-dodecanedioate (105.00 g, 406.4 mmol), γ-butyrolactone (8.75 g, 101.6 mmol), and a 28-wt % sodium methoxide in methanol solution (19.60 g, 101.6 mmol) was heated to 50° C. while being stirred. Into the solution, 550 g of n-hexane was added and was stirred while being cooled to 20° C. to form a suspension. The suspension was separated into a precipitate and a supernatant liquid using a pressure filter. The filtration residue was thoroughly washed with n-hexane.

The resulting filtration residue in an amount of 35.55 g was poured into 49.8 g (50.8 mmol) of an aqueous 10% phosphoric acid solution. Further, water (350 g) and 1,4-dioxane (250 g) were added, and the mixture was allowed to react for 5 hours at 100° C. The solution was separated into two layers. The organic layer was separated and the aqueous layer was extracted with toluene. The organic layer was mixed with the toluene extract and washed with water, and then the solvent was removed by distillation. As a result, 26.6 g of a crystal product was obtained. After isolation and purification, the crystal product was identified as methyl 15-hydroxy-12-keto-pentadecanoate corresponding to the compound represented by the general formula (7).

$^1$H-NMR (600 MHz, TMS, CDCl$_3$) 1.28 (12H, m, CH$_2$-4~9), 1.57 (2H, tt, J=7.3, 7.2, CH$_2$-10), 1.61 (2H, tt, J=7.3, 7.0, CH$_2$-3), 1.84 (2H, tt, J=6.7, 6.3, CH$_2$-14), 2.30 (2H, t, J=7.5, CH$_2$-2), 2.43 (2H, t, J=7.5, CH$_2$-11), 2.56 (2H, t, J=6.9, CH$_2$-13), 3.65 (2H, t, J=6.1, CH$_2$-15), 3.67 (3H, s, CH$_3$)

$^{13}$C-NMR (150 MHz, CDCl$_3$) 23.86 (CH$_2$-10), 24.92 (CH$_2$-3), 26.50 (CH$_2$-14), 29.09~29.36 (CH$_2$-4~9), 34.08 (CH$_2$-2), 39.48 (CH$_2$-13), 42.92 (CH$_2$-11), 51.40 (CH$_3$), 62.33 (CH$_2$-OH), 174.30 (C(=O)O), 211.76 (C=O)

According to gas chromatographic determination, the crystal product contains 79.3% of a compound represented by the general formula (7) (n=10, R=Me). The yield was 72.6% with respect to γ-butyrolactone.

Example 9

A condensation solution in an amount of 113.2 g (confirmed by quantitative analysis, after acidification of a part, that the solution contains 25.65 g of the condensation product and 80.84 g of the unreacted ester) prepared from dimethyl 1,12-dodecanedioate (105.00 g, 406.4 mmol), γ-butyrolactone (8.75 g, 101.6 mmol), and a 28-wt % sodium methoxide in methanol solution (19.60 g, 101.6 mmol) was heated to 50° C. while being stirred. Into the solution, 550 g of n-hexane was added and was stirred while being cooled to 20° C. to form a suspension. The suspension was separated into a precipitate and a supernatant liquid using a pressure filter. The filtration residue was thoroughly washed with n-hexane. The resulting filtration residue in an amount of 35.55 g was poured into 49.8 g (50.8 mmol) of an aqueous 10% phosphoric acid solution. Further, sodium dihydrogen-phosphate anhydride (13.63 g, 96.0 mmol), water (350 g) and 1,4-dioxane (250 g) were fed into the reaction vessel, and the mixture was allowed to react for 5 hours at 100° C. The solution was separated into two layers. The organic layer was separated and the aqueous layer was extracted with toluene. The organic layer was mixed with the toluene extract and washed with water, and then the solvent was removed by distillation. As a result, 26.56 g of a crystal product was obtained.

According to gas chromatographic determination, the crystal product contains 80.2% of a compound represented by the general formula (7) (n=10, R=Me). The yield was 73.3% with respect to γ-butyrolactone.

Reference Example 2

A compound represented by the general formula (7) (n=10, R=Me) (10.1 g, 35 mmol), sodium hydroxide (2.80 g, 0.07 mol), and water (25.2 g) were mixed and then refluxed while being heated for 4 hours. Into the mixture, 60 ml of diethylene glycol was added while continuing distillation. One hour later, 10.3 ml of 85%-hydrated hydrazine was added while stirring at 110° C. for 40 minutes. The temperature of the system was raised to 195 to 200° C., and then stirred for 16 hours at that temperature while removing the distilled components from the system. The solution was cooled, acidified with diluted sulfuric acid, and was extracted with chloroform. The chloroform layer was washed with water and dried with anhydrous magnesium sulfate, and the solvent was removed by distillation. As a result, 8.92 g of crystal product mixture was obtained.

According to gas chromatographic determination of tri-methylsilylated reaction mixture, the product mixture contains 97.2% of a compound represented by the general formula (5) (n=10). The yield from the compound represented by the general formula (1) (n=10, R=Me) was 96%.

Reference Example 3

Preparation of Reaction Mixture

A condensation solution prepared from dimethyl 1,12-dodecanedioate (105.00 g, 406.4 mmol), γ-butyrolactone (8.75 g, 101.6 mmol), and a 28-wt % sodium methoxide in methanol solution (19.60 g, 101.6 mmol) was heated to 50° C. while being stirred. Into the solution, 104.4 g of n-hexane was added, followed by stirring for 2 minutes. Next, 73.87 g of an aqueous 5.5%-NaOH solution was added while continuing stirring for 120 minutes. After the solution was allowed to stand for 5 minutes, it was separated into an organic layer and an aqueous layer. Into the aqueous layer, 19.00 g of an aqueous 41%-NaOH solution was added. After refluxing for two hours and cooling to 80° C., 126.52 g of a reaction mixture was obtained.

Example 10

Recovery of 1,18-dihydroxy-4,15-octadecanedione by Extraction

A part of the reaction mixture prepared in the above-mentioned REFERENCE EXAMPLE was extracted with the same weight of toluene for 20 minutes while maintaining the temperature at 80° C. This procedure was repeated five times, and the resulting organic layer and the aqueous layer were independently acidified with diluted sulfuric acid and then extracted with ethyl acetate. After washing the organic layer with a saturated sodium chloride solution, the solvent was distilled from the system to prepare a crystal product. Table 1 shows the results of HPLC determination of these layers.

TABLE 1

Results of Extraction of 1,18-dihydroxy-4,15-octadecanedione

| | Percent by weight in the mixture | Organic Layer | | Aqueous layer | |
|---|---|---|---|---|---|
| | | Weight | Recovery | Weight | Recovery |
| 15-hydroxy-12-ketopen-tadecanoic acid | 16.85 | 0.63 | 3.74 | 16.22 | 96.26 |
| dodecanedioic acid | 2.63 | 0.04 | 1.52 | 2.59 | 98.48 |
| 1,18-dihydroxy-4,15-octadecanedione | 1.74 | 1.73 | 99.43 | 0.01 | 0.57 |

Example 11

Purification of 15-hydroxy-12-ketopentadecanoic acid

The water content of the reaction mixture obtained in the REFERENCE EXAMPLE 3 was adjusted to 84%, and then the mixture was subjected to crystallization treatment for two hours in a thermostat vessel at 40° C. The precipitated crystal product was separated into a cake and a filtrate using a centrifugal filter. Water was added to cake at 40° C. to form a slurry, and the slurry was separated into a cake and a filtrate using a centrifugal filter. The filtrate was mixed with the former filtrate. The cake and the filtrate were acidified with diluted sulfuric acid and extracted with ethyl acetate. After washing the organic layer with a saturated sodium chloride solution, the solvent was removed by distillation to prepare a crystal product. Table 2 shows the results of HPLC determination of these layers.

TABLE 2

Results of Extraction of 1,18-dihydroxy-4,15-octadecanedione

| | Percent by weight in the mixture | Cake | | Filtrate | |
|---|---|---|---|---|---|
| | | Weight | Recovery | Weight | Recovery |
| 15-hydroxy-12-ketopen-tadecanoic acid | 16.85 | 0 | 0.00 | 16.85 | 100.00 |
| dodecanedioic acid | 2.63 | 0 | 0.00 | 2.63 | 100.00 |
| 1,18-dihydroxy-4,15-octadecanedione | 1.74 | 1.72 | 98.85 | 0.02 | 1.15 |

Example 12

Purification of 15-hydroxy-12-ketopentadecanoic acid

The reaction mixture obtained in the REFERENCE EXAMPLE 3 was maintained to 80° C., and extracted with the same weight of toluene for 20 minutes. This procedure was repeated five times, and the resulting aqueous layer was subjected to crystallization treatment for two hours in a thermostat vessel at 20° C. The precipitated crystal product was separated into a cake and a filtrate by a centrifugal filter. These were independently acidified with diluted sulfuric acid and extracted with ethyl acetate. After washing the organic layer with a saturated sodium chloride solution, the solvent was removed by distillation to prepare a crystal product. Table 3 shows the results of HPLC determination of these layers.

TABLE 3

Results of Purification of 15-hydroxy-12-ketopentadecanoic

| | Percent by weight in the mixture | Cake | | | Filtrate | |
|---|---|---|---|---|---|---|
| | | Weight | Recovery (%) | Purity in Crystal (%) | Weight | Recovery (%) |
| 15-hydroxy-12-ketopentadecanoic acid | 6.84 | 6.72 | 98.24 | 98.48 | 0.12 | 1.76 |

TABLE 3-continued

Results of Purification of 15-hydroxy-12-ketopentadecanoic

| | Percent by weight in the mixture | Cake | | | Filtrate | |
|---|---|---|---|---|---|---|
| | | Weight | Recovery (%) | Purity in Crystal (%) | Weight | Recovery (%) |
| dodecanedioic acid | 1.09 | 0.04 | 3.42 | 0.55 | 1.053 | 96.58 |

The results shown in Table 3 demonstrate that the crystal product separated before the sulfuric acid treatment 7.28 g of sodium 15-hydroxy-12-ketopentadecanoate and the filtrate contains 1.25 g of sodium dodecanedioate.

Example 13

Purification of 15-hydroxy-12-ketopentadecanoic Acid by pH Adjustment

The reaction mixture prepared in the above-mentioned REFERENCE EXAMPLE 3 was extracted with the same weight of toluene for 20 minutes while maintaining the temperature at 80° C. This procedure was repeated five times, and the resulting aqueous layer was subjected to crystallization treatment for 2 hours in a thermostat vessel at 20° C. The precipitated crystal product was separated into a cake and a filtrate using a centrifugal filter. The pH of the filtrate was adjusted to 6.5 with sulfuric acid, and the resulting crystal precipitate was separated into a cake and a filtrate using a centrifugal filter. The pH of filtrate was further adjusted to 3.0 with sulfuric acid, and a cake was obtained from the crystal product using a centrifugal filter. Table 4 shows the results of HPLC determination of these cakes.

TABLE 4

Results of Purification of 15-hydroxy-12-ketopentadecanoic acid by pH Adjustment

| | Percent by weight in the mixture | Cake at pH = 6.5 | | | Cake at pH = 3.0 | |
|---|---|---|---|---|---|---|
| | | Weight | Recovery (%) | Purity in Crystal (%) | Weight | Recovery (%) |
| 15-hydroxy-12-ketopentadecanoic acid | 0.24 | 0.23 | 95.35 | 99.5 | 0.011 | 4.65 |
| dodecanedioic acid | 2.11 | 0 | 0.00 | 0 | 2.11 | 100.00 |

Industrial Applicability

According to the present invention, 2-(ω-alkoxycarbonylalkanoyl)-4-butanolide and alkaline metal salt thereof can be obtained with high yield and satisfactory selectivity by an industrially advantageous production method using a dicarboxylate ester which is inexpensive and easily obtainable.

According to the present invention, an alkaline metal salt of 2-(ω-alkoxycarbonylalkanoyl)-4-butanolide and the derivative thereof, and the unreacted ester can be readily separated and purified with high yield and industrial advantages from the condensation solution obtained by the reaction of a dicarboxylate ester and the γ-butyrolactone.

In addition, according to the present invention, a novel ester of ω-hydroxy-(ω-3)-ketoaliphatic acid is obtained at high yield and with industrial advantages. The use of the ester of ω-hydroxy-(ω-3)-ketoaliphatic acid in the production of ω-hydroxyaliphatic acid being an important intermediate for large cyclic lactone-based perfumes does not require a macro amount of alkali and facilitates separation of water in the reaction system. Thus, a method useful for promoting industrial production with significantly reduced labor is provided.

According to the present invention, α,ω-dihydroxy-δ,(ω-3)-alkanedione, ω-hydroxy-(ω-3)-ketoaliphatic acid and a salt thereof, and dicarboxylic acid and a salt thereof can be effectively recovered with high selectivity by separation in the production of ω-hydroxy-(ω-3)-ketoaliphatic acid being an important intermediate for large cyclic lactone-based perfumes used in the perfume industry.

What is claimed is:

1. A method for separating and recovering an α, ω-dihydroxy-δ, (ω-3)-alkanedione represented by the general formula (9) comprising extracting the α, ω-dihydroxy-δ, (ω-3)-alkanedione represented by the general formula (9) with an organic solvent which is unreactive in basic conditions and insoluble in water from a mixture containing three compounds of an alkaline metal salt of ω-hydroxy-(ω-3)-ketoaliphatic acid represented by the general formula (5), an alkaline metal salt of a long-chain dicarboxylic acid represented by the general formula (8), and α,ω-dihydroxy-δ, (ω-3)-alkanedione represented by the general formula (9), or selectively crystallizing the α,ω-dihydroxy-δ-(ω-3)- alkanedione represented by the general formula (9) from the mixture:

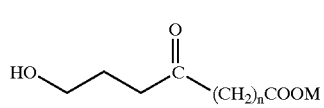
(5)

wherein n is an integer of 7 to 13 and M is an alkaline metal;

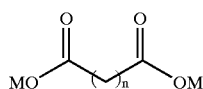
(8)

wherein n is an integer of 7 to 13 and M is an alkaline metal; and

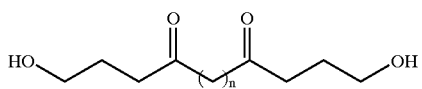
(9)

wherein n is an integer of 7 to 13.

2. A method for separating and recovering an alkaline metal salt of ω-hydroxy-(ω-3)-ketoaliphatic acid represented by the general formula (5) and an alkaline metal salt of a long-chain dicarboxylate represented by the general formula (8) comprising selectively crystallizing an alkaline metal salt of ω-hydroxy-(ω-3)-ketoaliphatic acid represented by the general formula (5) from a mixture prepared by separating and recovering an α, ω-dihydroxy-δ, (ω-3)-alkanedione represented by the general formula (9) comprising extracting the α, ω-dihydroxy-δ, (ω-3)-alkanedione represented by the general formula (9) with an organic solvent from a mixture containing three compounds of an alkaline metal salt of ω-hydroxy-(ω-3)-ketoaliphatic acid represented by the general formula (5), an alkaline metal salt of a long-chain dicarboxylic acid represented by the general formula (8), and α, ω-dihydroxy-δ, (ω-3)-alkanedione represented by the general formula (9), or selectively crystallizing the α, ω-dihydroxy-δ, (ω-3)-alkanedione represented by the general formula (9) from the mixture:

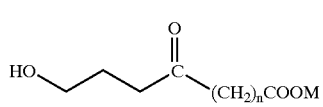
(5)

wherein n is an integer of 7 to 13 and M is an alkaline metal;

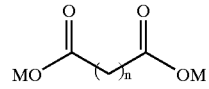
(8)

wherein n is an integer of 7 to 13 and M is an alkaline metal; and

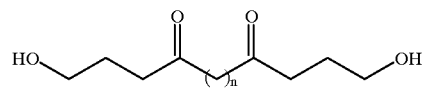
(9)

wherein n is an integer of 7 to 13, of the alkaline metal salt of ω-hydroxy-(ω-3)-ketoaliphatic acid represented by the general formula (5) and the alkaline metal salt of long-chain dicarboxylic acid represented by the general formula (8) and separating the mixture into a cake and a filtrate by solid-liquid separation.

3. A method for separating and recovering an α, ω-dihydroxy-δ, (ω-3)-alkanedione represented by the general formula (9) according to claim 1, wherein the organic solvent is selected from the group of benzene, toluene, xylenet, tetraline, decalin, pentane, hexane, heptane, octane, cyclohexane, isopropyl ether and dibutyl ether.

4. A method for separating and recovering an α, ω-dihydroxy-δ, (ω-3)-alkanedione represented by the general formula (9) according to claim 1, wherein the organic solvent is toluene.

* * * * *